United States Patent
Brogan et al.

(10) Patent No.: US 10,337,150 B2
(45) Date of Patent: *Jul. 2, 2019

(54) GRAFTED CROSSLINKED CELLULOSE USED IN ABSORBENT ARTICLES

(71) Applicant: The Procter & Gamble Company, Cincinnati, OH (US)

(72) Inventors: Karen Brogan, Federal Way, WA (US); Charles E. Miller, Federal Way, WA (US); Angel Stoyanov, Federal Way, WA (US); Torsten Lindner, Hessen (DE); Maike Siemons, Hessen (DE)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/807,916

(22) Filed: Jul. 24, 2015

(65) Prior Publication Data

US 2017/0022671 A1    Jan. 26, 2017

(51) Int. Cl.
  *A61F 13/53*    (2006.01)
  *A61L 15/28*    (2006.01)
  (Continued)

(52) U.S. Cl.
  CPC ........... *D21H 27/007* (2013.01); *A61F 13/53* (2013.01); *A61F 13/537* (2013.01); *A61L 15/28* (2013.01);
  (Continued)

(58) Field of Classification Search
  CPC .... D21H 27/002; D21H 27/007; D21H 11/20; A61L 15/24; A61L 15/28; A61L 15/22; A61L 15/42; A61L 15/60; A61F 13/00012
  See application file for complete search history.

(56) References Cited

U.S. PATENT DOCUMENTS 3,514,385 A * 5/1970 Magat ............... D06M 14/22
  522/89
3,656,884 A * 4/1972 Okaya ............... C08F 291/00
  525/309

(Continued)

FOREIGN PATENT DOCUMENTS

EP    1582624 A1 * 10/2005 ............. D21C 9/002
EP    1978140 B1 *  8/2014 ............. A61L 15/24
(Continued)

OTHER PUBLICATIONS

Yoshikuni Teramoto, Funtional Thermoplastic Materials from Derivatives of Cellulose and Related Structural Polysaccharides, Mar. 27, 2015, Molecules, No. 20, pp. 5487-5527.*

(Continued)

*Primary Examiner* — Jose A Fortuna
(74) *Attorney, Agent, or Firm* — Andrew J. Hagerty; Christian M. Best

(57) ABSTRACT

Grafted, crosslinked cellulosic materials used in absorbent articles, the grafted crosslinked cellulosic materials including cellulose fibers and polymer chains composed of at least one monoethylenically unsaturated acid group-containing monomer (such as acrylic acid) grafted thereto, in which one or more of the cellulose fibers and the polymer chains are crosslinked (such as by intra-fiber chain-to-chain crosslinks). Some of such materials are characterized by a wet bulk of about 10.0-17.0 cm$^3$/g, an IPRP value of about 1000 to 7700 cm$^2$/MPa·sec, and/or a MAP of about 7.0 to 38 cm H$_2$O. Methods for producing such materials may include grafting polymer chains from a cellulosic substrate, followed by treating the grafted material with a crosslinking agent adapted to effect crosslinking of one or more of the cellulosic substrate or the polymer chains.

9 Claims, 6 Drawing Sheets

(51) Int. Cl.
  *A61L 15/42* (2006.01)
  *D21H 11/20* (2006.01)
  *D21H 27/00* (2006.01)
  *A61F 13/537* (2006.01)
  *C08L 1/02* (2006.01)

(52) U.S. Cl.
  CPC .............. *A61L 15/42* (2013.01); *A61L 15/425* (2013.01); *D21H 11/20* (2013.01); *A61F 2013/530007* (2013.01)

(56) References Cited

U.S. PATENT DOCUMENTS

| | | | |
|---|---|---|---|
| 3,954,642 A * | 5/1976 | Schwuger | A47L 13/17 15/104.93 |
| 4,637,859 A | 1/1987 | Trokhan | |
| 4,865,596 A * | 9/1989 | Weisman | A61F 13/53 604/368 |
| 5,137,537 A | 8/1992 | Herron et al. | |
| 5,183,707 A | 2/1993 | Herron et al. | |
| 5,190,563 A | 3/1993 | Herron et al. | |
| 5,281,207 A * | 1/1994 | Chmielewski | A61F 13/535 604/368 |
| 5,607,414 A | 3/1997 | Richards et al. | |
| 5,700,254 A | 12/1997 | McDowall et al. | |
| 5,749,863 A * | 5/1998 | Payne | A61F 13/15203 428/378 |
| 5,814,570 A | 9/1998 | Cohen | |
| 5,998,511 A | 12/1999 | Westland et al. | |
| 6,068,620 A * | 5/2000 | Chmielewski | A61F 13/15658 604/358 |
| 6,184,271 B1 | 2/2001 | Westland et al. | |
| 6,534,149 B1 | 3/2003 | Daley et al. | |
| 6,620,865 B2 | 9/2003 | Westland et al. | |
| 6,844,066 B2 * | 1/2005 | Hamed | A61L 15/60 428/393 |
| 6,987,153 B2 | 1/2006 | Diehl et al. | |
| 7,786,341 B2 | 8/2010 | Schneider et al. | |
| 7,994,242 B2 | 8/2011 | Flohr et al. | |
| 8,722,797 B2 | 5/2014 | Stoyanov et al. | |
| 9,492,333 B2 * | 11/2016 | Uda | A61F 13/4756 |
| 2002/0123728 A1 | 9/2002 | Graf et al. | |
| 2004/0234760 A1 * | 11/2004 | Hamed | A61L 15/60 428/375 |
| 2005/0085150 A1 * | 4/2005 | Hamed | A61L 15/60 442/417 |
| 2007/0161308 A1 * | 7/2007 | Bourham | D06M 10/025 442/123 |
| 2007/0224161 A1 * | 9/2007 | Sun | A01N 37/28 424/78.27 |
| 2010/0211037 A1 * | 8/2010 | Gagliardi | A61F 13/53 604/370 |
| 2011/0077354 A1 * | 3/2011 | Stoyanov | D21C 9/002 525/54.21 |
| 2011/0259536 A1 * | 10/2011 | Flohr | A61L 15/24 162/2 |
| 2013/0137862 A1 * | 5/2013 | Stoyanov | D21C 9/007 536/56 |
| 2013/0209749 A1 | 8/2013 | Syangiro et al. | |
| 2014/0296765 A1 * | 10/2014 | Kipke | D06M 10/008 602/45 |
| 2015/0250664 A1 * | 9/2015 | Uda | A61F 13/531 604/370 |
| 2015/0297781 A1 * | 10/2015 | Uda | A61F 13/533 604/366 |
| 2017/0022314 A1 * | 1/2017 | Brogan | C08B 3/08 |
| 2017/0022671 A1 * | 1/2017 | Brogan | D21H 27/007 |
| 2017/0066865 A1 * | 3/2017 | Brogan | C08B 3/08 |

FOREIGN PATENT DOCUMENTS

| | | | | |
|---|---|---|---|---|
| EP | 3121313 A1 * | 1/2017 | | C08B 3/08 |
| GB | 1141271 A * | 1/1969 | | A61L 15/24 |
| GB | 1412002 A * | 10/1975 | | A61L 15/28 |
| WO | WO 9534329 A1 * | 12/1995 | | A61L 15/28 |
| WO | WO-2012057751 A1 * | 5/2012 | | A61L 15/28 |
| WO | WO-2017019516 A1 * | 2/2017 | | D21H 27/007 |

OTHER PUBLICATIONS

Gürdağ et al., "Cellulose Graft Copolymers: Synthesis, Properties, and Applications," Springer_Verlag Berlin Heidelberg, pp. 15-57. (Year: 2013).*

PCT International Search Report, dated Oct. 5, 2016 (12 pages).

* cited by examiner

GRAFTED CROSSLINKED CELLULOSE USED IN ABSORBENT ARTICLES

TECHNICAL FIELD

This disclosure relates to absorbent articles comprising cellulose fibers, and in particular to grafted, crosslinked cellulose.

BACKGROUND

Cellulosic fibers find utility in many applications, including absorbents. Indeed, cellulosic fibers are a basic component of many absorbent articles such as diapers. The fibers form a liquid absorbent structure, a key element in an absorbent article.

Cellulosic fluff pulp, a form of cellulosic fibers, has been used for absorbent applications because the fluff pulp form provides a high void volume, or high bulk, liquid absorbent fiber structure. However, this structure tends to collapse upon wetting, which reduces the volume of liquid that can be retained in the wetted structure. Further, such collapse may inhibit transfer of liquid into unwetted portions of the cellulose fiber structure, leading to local saturation.

Whereas the ability of an absorbent article containing cellulosic fibers to initially acquire and distribute liquid (such as from an initial liquid insult) relates to the article's dry bulk and capillary structure, the ability of a wetted structure to acquire additional liquid (such as from subsequent and/or extended liquid insults) relates to the structure's wet bulk. Due to diminished acquisition and capacity properties related to loss of fiber bulk associated with liquid absorption, the potential capacity of a dry high bulk fiber structure such as cellulosic fluff pulp may not be fully realized, with the liquid holding capacity instead determined by the structure's wet bulk.

Intra-fiber crosslinked cellulose fibers and structures formed therefrom generally have enhanced wet bulk as compared to non-crosslinked fibers. The enhanced bulk is a consequence of the stiffness, twist, and curl imparted to fibers as a result of crosslinking. Accordingly, crosslinked fibers are incorporated into absorbent articles to enhance their wet bulk and liquid acquisition rate.

In addition to wet bulk and liquid acquisition rate, a material's suitability for use in absorbent articles may be characterized in terms of other performance properties, such as liquid permeability. As noted above, performance properties tend to result from different fiber characteristics such as fiber length, fiber stiffness, and so forth. However, relationships between some performance properties indicate the existence of trade-off trends for many cellulose fiber (and other) materials. For example, liquid permeability tends to decrease as capillary pressure, expressed in terms of medium absorption pressure, increases. As explained in greater detail below, this particular relationship manifests in a manner that can be mathematically approximated as a power curve function of the two properties, which is characteristic for many if not all materials used in absorbent applications, including cellulose fiber materials, synthetic fiber materials, blends, and so forth. Of these materials, the "trade-off" curve for cellulose fiber products is the highest, but successful efforts to raise this curve higher—that is, to produce materials that exhibit better liquid permeability value at a given capillary pressure value (and vice versa) than as predicted by the power curve function described by cellulose fibers—have not yet been observed.

There are a number of methods for preparing crosslinked cellulose fibers; several are summarized in U.S. Pat. No. 5,998,511 to Westland, et al. Much effort has been spent improving crosslinking processes, such as to lower production and/or material costs, to modify absorbent and/or other fiber properties of the products, and so forth. In one example, polycarboxylic acids have been used to crosslink cellulosic fibers (such as in U.S. Pat. Nos. 5,137,537, 5,183,707, and 5,190,563, all to Herron, et al., and so forth), to produce absorbent structures containing cellulosic fibers crosslinked with a C2-C9 polycarboxylic acid. Despite advantages that polycarboxylic acid crosslinking agents provide, cellulosic fibers crosslinked with low molecular weight (monomeric) polycarboxylic acids, such as citric acid, have been found to undergo reversion to a non-crosslinked condition and thus have a useful shelf-life that is relatively short. Polymeric polycarboxylic acid crosslinked fibers, however, such as disclosed in U.S. Pat. Nos. 5,998,511, 6,184,271, and 6,620,865, all to Westland, et al., amongst others, resist such aging or reversion, due in part to the participation of the polymeric polycarboxylic acid molecule in the crosslinking reaction with an increased number of reactive carboxyl groups than is the case with monomeric polycarboxylic acids such as citric acid. In another example, U.S. Pat. No. 8,722,797 to Stoyanov, et al., discloses the use of a comparatively low molecular weight polyacrylic acid having phosphorous (in the form of a phosphinate) incorporated into the polymer chain as a crosslinking agent to achieve crosslinked cellulose fibers having improved brightness and whiteness (as well as other properties) as compared to those prepared with higher molecular weight phosphinated agents or polyacrylic acid agents without phosphinates.

Thus, there is a continuing need to produce crosslinked cellulose fibers and compositions and materials including such fibers for use in absorbent articles.

SUMMARY

Crosslinked cellulosic materials composed of a cellulosic substrate, such as cellulose fibers, having grafted polymer chains, with such cellulose fibers and/or grafted polymer chains being crosslinked, and methods of producing such compositions, are disclosed herein for use in absorbent articles. The fibrous materials produced according to the present disclosure are also referred to herein as "grafted crosslinked cellulose" and may be described as "compositions" as well as "materials." In the grafted crosslinked cellulose of the present disclosure, the polymer chains may be composed of monoethylenically unsaturated acid group-containing monomers (non-limiting examples include acrylic acid, maleic acid, methacrylic acid, etc., and combinations thereof), which may be crosslinked in a variety of manners (non-limiting examples include ester intra-fiber crosslinks via crosslinking agents such as homopolymers, hyperbranched polymers, pentaerythritol, and so forth).

Acrylic acid may be used as the monoethylenically unsaturated acid group-containing monomer. The graft yield may be from 5 to 35 weight %, and more particularly from 10 to 20 weight %. The wet bulk may be at least 6% greater, and up to at least 40% greater, than untreated cellulose (referring to the cellulose substrate in an untreated, i.e., non-grafted and non-crosslinked, state). The wet bulk may be from about 10.0 to about 17.0 cm$^3$/g, and more particularly from about 15.0 to about 17.0 cm$^3$/g. The intra-fiber chain-to-chain crosslinks may be mainly composed of a crosslinking agent such as pentaerythritol or a hyperbranched polymer. Some embodiments include intra-fiber chain-to-cellulose crosslinks.

The material may be characterized by an IPRP value of about 1000 to 7700 cm²/MPa·sec and/or a MAP of about 7.0 to 20 cm H₂O. In the power curve function, for a given IPRP value y (in cm²/MPa·sec) from 1000 to 7700, the MAP value of the material (in cm H₂O) may be within +/−30% of the value of x in the formula $y=mx^z$; wherein m is from 600 to 1200, and wherein z is from −0.590 to −0.515. More particularly z may be from −0.560 to −0.520 and/or m may be from 800 to 1100. At a given IPRP value (in cm²/MPa·sec) from 800 to 5400, the material may have a MAP value that is equal to or higher (e.g., 0-20% higher) than the corresponding MAP value possessed by non-grafted, crosslinked cellulose fiber, and/or at a given MAP value (in cm H₂O) from 7.0 to 20, the material may have an IPRP value that is equal to or higher (e.g., 0-15% higher) than the corresponding IPRP value possessed by non-grafted, crosslinked cellulose fiber. The IPRP value may be 5400 cm²/MPa·sec or above.

Example methods of producing grafted crosslinked cellulose in accordance with the present disclosure for use in absorbent articles include grafting polymer chains of at least one monoethylenically unsaturated acid group-containing monomer from a cellulosic substrate to produce a grafted cellulosic material, followed by crosslinking the grafted cellulosic material by treating the material with a crosslinking agent adapted to effect crosslinking of one or more of the cellulosic substrate or the polymer chains. In some methods, the grafting is performed in situ and may include reacting the monomer with the cellulosic substrate in the presence of a grafting initiator such as cerium(IV) sulfate. In some methods, acrylic acid is used as the monomer. Some methods include varying the amounts of the initiator and/or the ratio of cellulose to monomer to achieve a desired graft level.

Such methods may include any of a variety of crosslinking procedures. Some methods include establishing intra-fiber crosslinks via an esterification reaction via one or more crosslinking agents such as pentaerythritol, a polymeric crosslinking agent (for example, a homopolymer formed of the at least one monoethylenically unsaturated acid group-containing monomer), a hyperbranched polymer, and so forth. Some methods include establishing intra-fiber crosslinks via an ionic reaction via a multivalent inorganic compound (such as aluminum sulfate) as a crosslinking agent. Some methods include establishing intra-fiber crosslinks via a radical reaction via a suitable inorganic salt (such as ammonium persulfate) as a cross-linking agent. Some methods include at least partially neutralizing the grafted polymer side chains by treating the grafted cellulosic material with an alkaline solution.

The materials, concepts, features, and methods briefly described above are clarified with reference to the detailed description below.

DETAILED DESCRIPTION

Grafted Cross-Linked Cellulose

Figure 1:
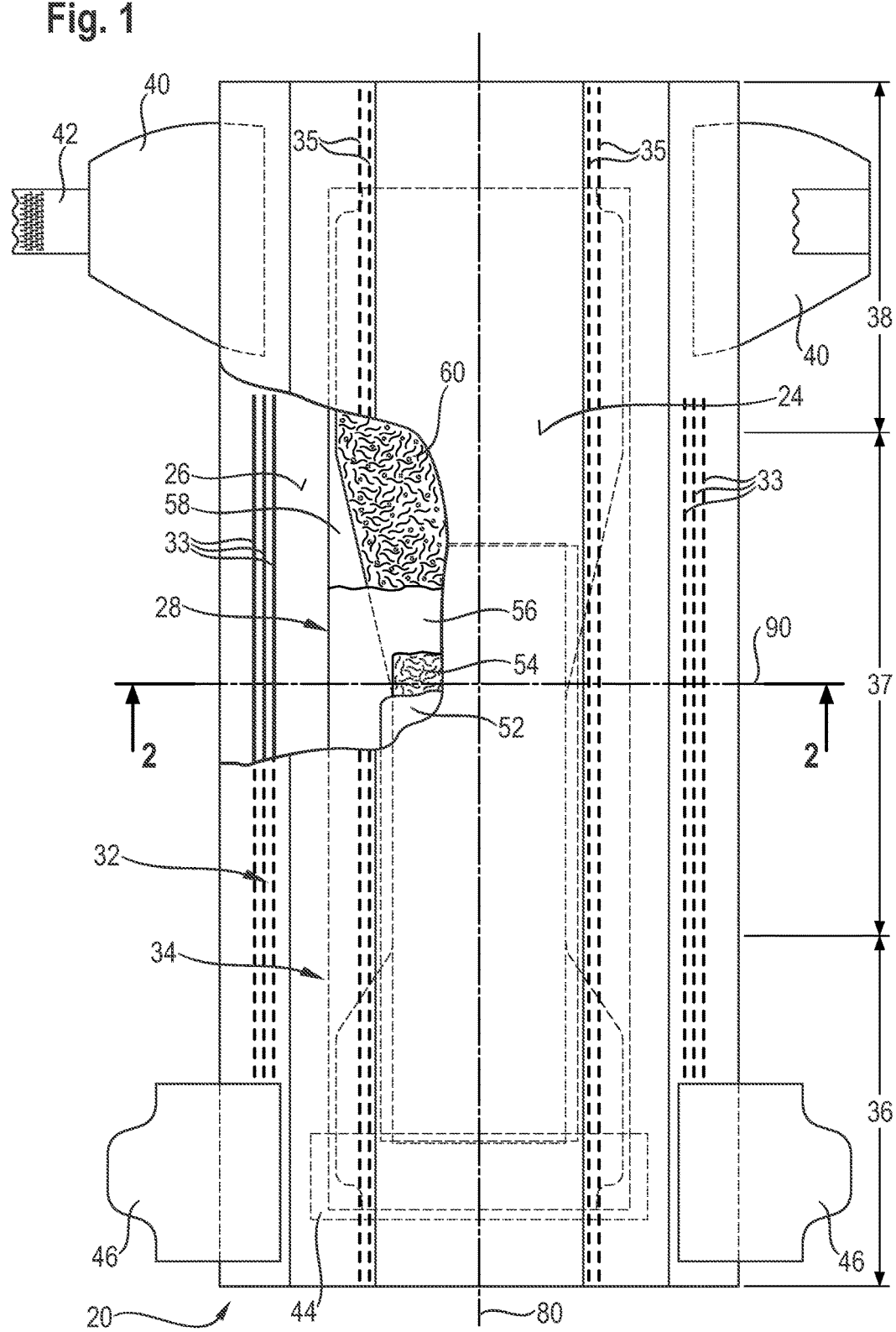
FIG. 1 is a top view of an exemplary absorbent article in the form of a diaper according to the invention, with some layers partially removed.

There has been much research on grafting copolymers, including grafting copolymers from cellulosic materials, such as with grafting polymer chains or "arms" consisting of acrylic acid monomers, from holocellulose (see, e.g., Okieimen, E. F., and Ebhoaye, J. E., *Grafting Acrylic Acid Monomer on Cellulosic Materials*, J. Macromol. Sci.-Chem., pp 349-353 (1986)). However, there has been no investigation of subjecting grafted cellulose structures to conditions suitable to effect crosslinking in non-grafted cellulose materials.

The inventors have discovered, however, that various absorbent and other properties of certain grafted cellulose structures are changed upon undergoing crosslinking by various reactions and mechanisms. In particular, absorbent properties of some grafted, crosslinked cellulose structures, such as wet bulk, absorbent capacity, permeability (e.g., in-plane radial permeability or IPRP), capillary pressure (e.g., as measured by medium absorption pressure or MAP), as described in greater detail below, are consistent with or improved relative to those achieved by crosslinked cellulose products produced by other methods, and are favorable when compared to cellulose fibers that are not crosslinked and/or not grafted.

As an example of a non-crosslinked, non-grafted cellulose fiber, a bleached kraft pulp product available from Weyerhaeuser NR Company under the designation CF416 has a wet bulk of 11.71 cm³/g and an absorbent capacity of 11.75 g/g. When grafted with polymer chains composed of monoethylenically unsaturated acid group-containing monomers (with a graft yield in the range of about 5-35 weight %) the resulting grafted CF416 exhibited lower wet bulk values (of about 9.8-11.2 cm³/g, with acrylic acid used as the graft species) and absorbent capacity values (of 10.0-11.3 g/g, with acrylic acid used as the graft species), but when subjected to subsequent crosslink treatment, the grafted, crosslinked cellulose structures produced in accordance with the present disclosure exhibited improved wet bulk values of about 15.0-17.0 cm³/g, and/or absorbent capacity values of about 15.0-17.0 g/g. A crosslinked (and non-grafted) fiber product available from Weyerhaeuser NR Company under the designation CMC530, useful as a control, has a wet bulk of approximately 16.4 cm³/g and an absorbent capacity of 16.5 g/g. Accordingly, the grafted, crosslinked cellulose fibers of the present disclosure may have suitability, for example, in absorbent applications, especially absorbent articles, similar to those for which non-grafted crosslinked cellulose fibers are used.

As another example of this suitability, the grafted cellulose structures produced in accordance with the present disclosure typically exhibit IPRP and/or MAP values consistent with or improved relative to non-grafted cellulose fibers. As explained in greater detail below, IPRP and MAP values indicate a trade-off relationship that approximates a power law function of the two properties. IPRP and MAP values relating to CMC530 and other non-grafted controls as compared to that of example embodiments of grafted cellulose structures indicate that the grafted, crosslinked structures can exhibit (or are predicted to exhibit, according to formulae expressing best-fit curves generated by measured IPRP and MAP data) comparable or increased values, up to 15 or 20%, or even greater.

Cellulosic fibers useful for making the grafted crosslinked cellulose of the present disclosure are derived primarily from wood pulp. Although suitable wood pulp fibers may be obtained from chemical processes such as the kraft and sulfite processes, with or without subsequent and/or prior mercerization and/or bleaching, the pulp fibers may also be processed by thermomechanical or chemithermomechanical methods, or various combinations thereof. Ground wood fibers, recycled or secondary wood pulp fibers, and bleached and unbleached wood pulp fibers may be used. One example starting material is prepared from long-fiber coniferous wood species, such as southern pine, Douglas fir, spruce, hemlock, and so forth. Details of the production of wood pulp fibers are known to those skilled in the art. Suitable fibers are commercially available from a number of sources, including the Weyerhaeuser NR Company. For example, suitable cellulose fibers produced from southern pine that may be used as the cellulose substrate in the materials of the present disclosure are available from the Weyerhaeuser NR Company under the designations CF416, CF405, NF405, NB416, FR416, FR516, PW416, and PW405, amongst others.

The graft species suitable for grafting to the cellulosic fiber "backbone" to produce the grafted crosslinked cellulose materials of the present disclosure include those that may be described as monoethylenically unsaturated acid group-containing monomers, which include, for example, acrylic acid, methacrylic acid, crotonic acid, isocrotonic acid, maleic acid, fumaric acid, itaconic acid, vinylsulfonic acid, 2-acrylamido-2-methyl-1-propane sulfonic acid, vinyl acetic acid, methallyl sulfonic acid, and so forth, as well as their alkali and/or ammonium salts, and various combinations of the aforementioned examples. The choice of suitable graft species is guided in part by the nature of the backbone from which the grafted arms are grown, achieving a suitable polymer architecture, the desired end result of the crosslink treatment, and so forth.

For example, grafting, in the context of polymer chemistry, refers in general to the synthesis of polymer chains attached to a substrate, and thus encompasses mechanisms such as "grafting to," which refers to a polymer chain adsorbing onto a substrate out of solution, as well as "grafting from," which refers to initiating and propagating a polymer chain (such as by step-growth addition of monomer units) at a grafting site on the substrate. The latter mechanism is generally considered to offer greater control over the resulting polymer architecture, density of grafting sites, polymer chain lengths and linearity, and so forth. Considering these factors, graft species that include one or more acid groups are chemically appropriate when considered against a goal of establishing intra-fiber crosslinks, such as chain-to-chain crosslinks between grafted arms of an individual cellulose fiber. Further, monoethylenenically unsaturated graft species are suitable for the grafted crosslinked cellulose materials herein because of their ability to graft to a cellulose substrate without creating additional branches or side chains (as opposed, for example, to species with more than one unsaturated group, the use of which is more difficult to control). Monomeric graft species are considered to be easier to control, in terms of reactivity, density of polymer chains, establishing desired chain lengths and polymer chain architectures (e.g., linear, unbranched polymers grafted at one end to the cellulose backbone), suppressing crosslink reactions from occurring in the grafting stage, and so forth.

"Grafting," as the term is used herein, refers collectively to the processes of initiation, growth, and termination of growth polymerization of the (monomeric) graft species from one or more grafting sites on the cellulosic substrate. Typically, grafting according to methods discussed herein is performed in situ, in which an initiator is used, such as to create active centers on the substrate and, usually to a lesser extent, initiate homopolymerization in the aqueous phase. As such, although the grafting processes described herein proceed mainly by way of the "grafting from" mechanism described above, the term does not exclusively refer to this mechanism. Rather, "grafting" also encompasses the "grafting to" mechanism, other mechanisms, and/or combinations thereof. Moreover, the terms "to" and "from," when used when referring to grafting, do not exclusively refer to the corresponding grafting mechanism, but instead may each encompass some degree of the other grafting mechanism (or mechanisms).

It was found that by controlling the amount of graft species used, various levels of grafting were obtained, characterized by graft yield %, defined below as the additional weight of a grafted sample attributable to the polymerized graft species. For example, acrylic acid readily grafted from cellulose up to approximately 30% graft yield. Additionally, by varying the levels (e.g., weight %) of initiator, the number of graft sites available on the cellulosic substrate was altered. Variations in graft yield were also obtained by varying the ratio of cellulose to graft species.

In general, grafted cellulose fibers were produced in situ by dissolving a measured amount of initiator, such as cerium(IV) sulfate, in deionized water, and then dissipating a designated amount of graft species, such as 4-60 weight % acrylic acid (based on the oven-dry weight of the cellulose), in the solution. The levels of cerium(IV) sulfate initiator were varied between about 4.5-7.0 weight % (based on the oven-dry weight of the cellulose). The grafting solution was added to the cellulosic substrate, the treated cellulose was allowed to react, then washed and filtered to remove unreacted grafting solution and excess homopolymers of the graft species, dried, and weighed to determine graft yield %. In some examples, cellulose-graft-poly(acrylic) acid was then treated with dilute solutions of sodium hydroxide to at least partially neutralize the grafted arms on the cellulosic substrate.

A variety of cross-linking agents and reaction mechanisms were applied to various grafted cellulose materials, including ionic crosslinking reactions using multivalent inorganic compounds (such as aluminum sulfate, a trivalent salt, and titanium-based crosslinking agents), covalent ester crosslinking reactions using polymeric crosslinking agents (for example, a homopolymer of the graft species, such as poly(acrylic) acid or "PAA" when acrylic acid was used as the graft species), pentaerythritol, and various hyperbranched polymers ("HPB"), and a radical-based crosslinking mechanism using ammonium persulfate. Each was performed, at various levels, on various graft yield levels of fiberized, grafted cellulose and/or partially neutralized grafted cellulose, with various factors determining the conditions and amounts of reagents selected (e.g. solubility in water, ability to distribute evenly across the grafted cellulose, etc.).

In general, the grafted structures assumed a polymer architecture consisting mainly of linear, unbranched polymer chain arms attached to the cellulose backbone at one end. When subjected to the various cross-linking reactions, the resulting crosslinked, grafted structures generally exhibited intra-fiber crosslinks between grafted arms (such as via pentaerythritol, or a hyperbranched polymer), also referred to as chain-to-chain crosslinks. Additionally, in some cases, for example when treated with polymeric crosslinking agents, some of the chain arms attached to the cellulose backbone at more than one point, also referred to as chain-to-cellulose crosslinks, and some polymer bonded along the cellulose backbone. While not being bound by theory, it is believed that the stiffness and resiliency imparted by establishing intra-fiber chain-to-chain and/or chain-to-cellulose crosslinks strengthen the high void volume structure and provide the observed, improved absorbent properties as compared to non-crosslinked grafted cellulose fibers and non-crosslinked, non-grafted cellulose fibers.

Although the methods disclosed herein primarily establish intra-fiber crosslinks (such as chain-to-chain crosslinks between grafted arms of an individual cellulose fiber, chain-to-cellulose crosslinks between a grafted arm of a cellulose fiber to elsewhere on the cellulose fiber, and so forth), some materials also exhibited a minor degree of inter-fiber crosslinking, such as between separate cellulose fibers and/or grafted chains thereon. In general, inter-fiber crosslinking is thought to increase the number of "knots" in the resulting fibers. Although a higher knot content is generally not considered to be a desirable characteristic in cellulosic material used in absorbent applications (both for the sake of overall product appearance, as well as for the comparative ease of processing lower knot content fibers), a greater degree of inter-fiber crosslinking may be achieved by using the processes described herein, such as, for example, by applying and curing the crosslinking agent to cellulose in sheet form, rather than to fiberized cellulose. Other variations may include selecting graft species and/or crosslinking agent(s) appropriate for establishing such inter-fiber crosslinking, suitably varying process conditions, and so forth, to achieve a desired amount of inter-fiber crosslinking. All of such variations are considered to be within the scope of this disclosure.

Absorbent Articles

The grafted crosslinked cellulose produced in accordance with the present disclosure are incorporated in absorbent articles. "Absorbent articles" refers to products that absorb and contain body exudates, and, more specifically, refers to products that are placed against or in proximity to the body of the wearer to absorb and contain the various exudates discharged from the body. Absorbent articles include diapers and pants (to be worn by babies, infants and/or adults), absorbent inserts for diapers or pants, feminine care absorbent articles such as sanitary napkins and pantiliner, breast pads and the like. The term "absorbent article" as used herein also refers to disposable products such as care mats, bibs, wipes (dry and wet wipes) for personal hygiene as well as to paper products.

As used herein, the term "body exudates" includes, but is not limited to, urine, blood, vaginal discharges, breast milk, sweat and fecal matter.

The absorbent articles of the present invention are disposable. Disposable absorbent article refers to an article that is disposed or discarded after a limited number of usage events over varying lengths of time, for example, less than 5 events, less than 2 events, or less than 2 events. Typically, the disposable absorbent article is intended to be disposed after single use.

Generally, absorbent articles which are placed against or in proximity to the body of a wearer, such as diapers, pants and feminine hygiene products, may comprise a topsheet, backsheet, an absorbent core and optionally an acquisition-distribution system, which may consist of one or more layers, such as an upper layer towards the topsheet and a lower layer towards the backsheet. The absorbent core is normally placed between the backsheet and the topsheet, the optional acquisition-distribution system is typically placed between the absorbent core and the topsheet. The grafted crosslinked cellulose described herein may be comprised by the absorbent core and/or by the acquisition-distribution system of the absorbent article. For example, one or more layers, such as the lower layer, of the acquisition-distribution system may comprise or may consist of the grafted crosslinked cellulose. Also, for single layer acquisition-distribution system, the single layer may comprise or may consist of the grafted crosslinked cellulose. Where the grafted crosslinked cellulose are comprised by the absorbent core, the absorbent core may further comprise other absorbent material, such as non-cross-linked cellulose fibers (pulp fibers), superabsorbent polymer (e.g. in particulate form) or combinations thereof. The absorbent core may comprise from 10 wt % to 100 wt %, or from 20 wt % to 80 wt % of the grafted crosslinked cellulose disclosed herein.

"Diaper" and "pant" refers to an absorbent article generally worn by babies, infants and incontinent (adult) persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

A "feminine care absorbent article" is a personal care product used by women during menstruation to absorb and retain menses, vaginal discharge, and other bodily functions related to vulva. Feminine care absorbent articles include pantiliners and sanitary napkins. The term "sanitary napkin" as used herein refers to an absorbent article which is worn by females adjacent to the pudendal region that is intended to absorb and contain the various exudates which are discharged from the body. The term "pantiliner" as used herein refers to an absorbent article that is less bulky than a sanitary napkin and is generally worn by women between their menstrual periods.

A "paper product" refers to a wet-formed fibrous structure comprising cellulose fibers, such as the grafted crosslinked cellulose disclosed herein. Paper products include tissue-towel paper products, such as toilet tissue and paper towels, table napkins, bath tissue and the like. A tissue-towel paper product might for example be a conventional felt-pressed or conventional wet-pressed tissue paper. Examples of paper products are disclosed in US2013/0209749 and U.S. Pat. No. 4,637,859.

Figure 2:
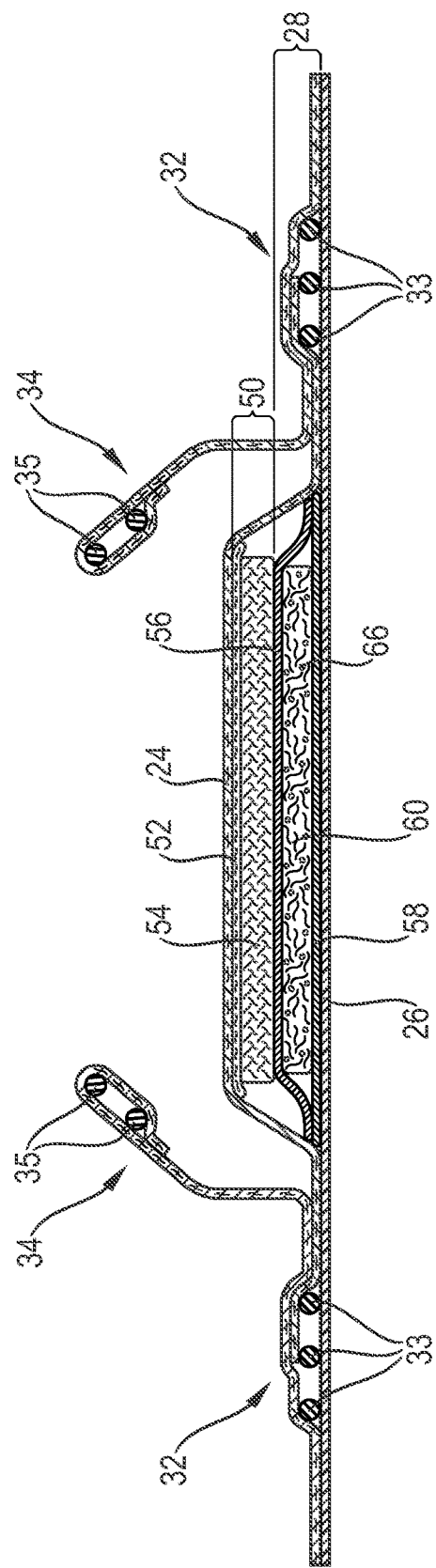
FIG. 2 is a transversal cross-section of the diaper of FIG. 1.

A typical disposable absorbent article of the present invention that is placed against or in proximity to the body of the wearer to absorb and contain the various exudates discharged from the body, is represented in FIGS. 1 and 2 in the form of a diaper 20.

In more details, FIG. 1 is a plan view of an exemplary diaper 20, in a flat-out state, with portions of the diaper being cut-away to more clearly show the construction of the diaper 20. This diaper 20 is shown for illustration purpose only as the structure of the present invention may be comprised in a wide variety of diapers or other absorbent articles.

As shown in FIGS. 1 and 2, the absorbent article, here a diaper, can comprise a liquid pervious topsheet 24, a liquid impervious backsheet 26, an absorbent core 28 which is positioned between f the topsheet 24 and the backsheet 26. The absorbent core 28 can absorb and contain liquid received by the absorbent article and may comprise absorbent materials 60, such as superabsorbent polymer particles 66 and/or cellulose fibers, as well as other absorbent and non-absorbent materials commonly used in absorbent articles (e.g. thermoplastic adhesives immobilizing the superabsorbent polymer particles). The absorbent material and non-absorbent material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbent articles of the invention, especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers. In the examples below, the ADS 50 comprises two layers: a distribution layer 54 and an acquisition layer 52 disposed between the absorbent core and the topsheet.

The ADS may be free of superabsorbent polymer. The prior art discloses many types of acquisition-distribution systems, see for example WO2000/59430, WO95/10996, U.S. Pat. No. 5,700,254, WO02/067809.

The function of a distribution layer 54 is to spread the insulting fluid liquid over a larger surface within the article so that the absorbent capacity of the absorbent core can be more efficiently used. Distribution layers may be made of a nonwoven material based on synthetic or cellulosic fibers and having a relatively low density. The distribution layer may typically have an average basis weight of from 30 to 400 g/m$^2$, in particular from 80 to 300 g/m$^2$.

The distribution layer may for example comprise at least 50%, or 60%, or 70%, or 80%, or 90% by weight of cross-linked cellulose fibers, such as the grafted crosslinked cellulose disclosed herein. The distribution layer may also consist completely of the grafted crosslinked cellulose disclosed herein The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the core with a relatively high void volume, permeability and liquid absorption, and hence reduced leakage and improved dryness.

The distribution layer comprising cross-linked cellulose fibers, such as the grafted crosslinked cellulose disclosed herein, may comprise other fibers, but this layer may advantageously comprise at least 50%, or 60%, or 70%, or 80%, or 90% or even up to 100%, by weight of the layer, of cross-linked cellulose fibers such as the grafted crosslinked cellulose disclosed herein. The at least 50%, or 60%, or 70%, or 80%, or 90% or even up to 100%, by weight of the layer, of cross-linked cellulose fibers may also be a mixture of the grafted crosslinked cellulose disclosed herein and other crosslinked cellulose fibers, and such mixture may comprise at least 50%, or at least 60% by weight of the mixture of the grafted crosslinked cellulose disclosed herein. Examples of mixed layers of cross-linked cellulose fibers and other materials may comprise 70% by weight of chemically cross-linked cellulose fibers (such as the grafted crosslinked cellulose disclosed herein), 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the mixed layers of cross-linked cellulose fibers and other materials may comprise 68% by weight chemically cross-linked cellulose fibers (such as the grafted crosslinked cellulose disclosed herein), 16% by weight untreated pulp fibers, and 16% by weight PET fibers.

The absorbent article 20 may further comprise an acquisition layer 52, whose function is to quickly acquire the fluid away from the topsheet so as to provide a good dryness for the wearer. The acquisition layer 52 is typically placed directly under the topsheet and below the distribution layer. The acquisition layer may typically be or comprise a nonwoven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

The diaper may also comprise elasticized leg cuffs 32 and barrier leg cuffs 34, which provide improved containment of liquids and other body exudates especially in the area of the leg openings. Usually each leg cuffs 32 and barrier cuffs 34 will comprise one or more elastic string 33 and 35, represented in exaggerated form on FIGS. 1 and 2. Moreover, the diaper 20 may comprise other features such as back ears 40, front ears 46 and/or barrier cuffs 34 attached to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 1 and 2 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

Feminine Care Absorbent Article

A feminine care absorbent article generally comprises at least a backsheet, a topsheet which is joined to the backsheet, and typically an absorbent structure disposed between the backsheet and the topsheet.

A pantiliner generally has two end regions and a middle region (i.e. a crotch region). The pantiliner has a body-facing surface and a garment facing surface.

The size and shape of the absorbent structure positioned between the topsheet and the backsheet can be altered to meet absorbent capacity requirements, and to provide comfort to the wearer. The absorbent structure suitable for use in the present invention can be any liquid-absorbent material known in the art for use in absorbent articles. The absorbent structure may comprise or consist of the grafted crosslinked cellulose disclosed herein.

While the pantiliner may have any shape known in the art, a typical shape is generally "hourglass" shaped.

The garment facing surface of the pantiliner can have thereon pressure sensitive adhesive for affixing to a wearer's undergarments. Typically, such adhesive is covered with a release strip which is removed before affixing to the undergarment.

Pantiliners can also be provided with lateral extensions known commonly in the art as "flaps" or "wings" (not shown) intended to extend over and cover the panty elastics in the crotch region of the user's undergarment. However, wings are normally not used with pantiliners but are more often used in sanitary napkins.

Paper Product

A paper product generally comprises are consists of a fibrous structure. The fibrous structures can be single-ply or multi-ply fibrous structures and can comprise cellulosic pulp fibers. Especially, the fibrous structure can comprise or consist of the grafted crosslinked cellulose disclosed herein. Other naturally-occurring and/or non-naturally occurring fibers can also be present in the fibrous structures. The fibrous structures can be throughdried, or "through air dried (TAD)". The fibrous structures can be wet-laid fibrous structures. The fibrous structures can be incorporated into single- or multi-ply paper products. The paper products can be in roll form where they are convolutedly wound or wrapped about themselves with or without the employment of a core. Alternatively, the paper products or fibrous structures can be in sheet form or can be at least partially folded over themselves.

Test Methods

AFAQ Analysis

Some performance properties of the grafted, crosslinked cellulosic compositions according to the present disclosure—specifically, absorbent properties of wet bulk, wick time, wick rate, and absorbent capacity—were determined using the Automatic Fiber Absorption Quality (AFAQ) Analyzer (Weyerhaeuser Co., Federal Way, Wash.), according to the following procedure:

A dry 4-gram sample of the pulp composition is placed through a pinmill to open the pulp, and then airlaid into a tube. The tube is then placed in the AFAQ Analyzer. A plunger then descends on the airlaid fluff pad at a pressure of 0.6 kPa. The pad height is measured, and the pad bulk (or volume occupied by the sample) is determined from the pad height.

The weight is increased to achieve a pressure of 2.5 kPa and the bulk recalculated. The result is two bulk measurements on the dry fluff pulp at two different pressures.

While the dry fluff pulp is still compressed at the higher pressure, water is introduced into the bottom of the tube (to the bottom of the pad), and the time required for water to wick upward through the pad and reach the plunger (defined as wick time) is measured. The bulk of the wet pad at 2.5 kPa is also calculated. From distance measurements used to calculate the bulk, the wick rate is determined by dividing the wick time by the distance traveled by the water (e.g. the height of the wetted fluff pad). The plunger is then withdrawn from the tube and the wet pad is allowed to expand for 60 seconds. In general, the more resilient the sample, the more it will expand to reach its wet rest state. Once expanded, this resiliency is measured by reapplying the plunger to the wet pad at 0.6 kPa and determining the bulk. The final bulk of the wet pad at 0.6 kPa is considered to be the "wet bulk at 0.6 kPa" (in $cm^3/g$, indicating volume occupied by the wet pad, per weight of the wet pad, under the 0.6 kPa plunger load) of the pulp composition. When the term "wet bulk" is used herein, it refers to "wet bulk at 0.6 kPa" as determined according to this procedure.

Absorbent capacity is calculated by weighing the wet pad after water is drained from the equipment and reported as grams water per gram dry pulp.

IPRP Analysis

Permeability generally refers to the quality of a porous material that causes it to allow liquids or gases to pass through it and, as such, is generally determined from the mass flow rate of a given fluid through it. The permeability of an absorbent structure is related to the material's ability to quickly acquire and transport a liquid within the structure, both of which are key features of an absorbent article. Accordingly, measuring permeability is one metric by which a material's suitability for use in absorbent articles may be assessed.

The following test is suitable for measurement of the In-Plane Radial Permeability (IPRP) of a porous material.

The quantity of a saline solution (0.9% NaCl) flowing radially through an annular sample of the material under constant pressure is measured as a function of time.

Testing is performed at 23° C.±2C.° and a relative humidity 50%±5%. All samples are conditioned in this environment for twenty four (24) hours before testing.

Figure 3:
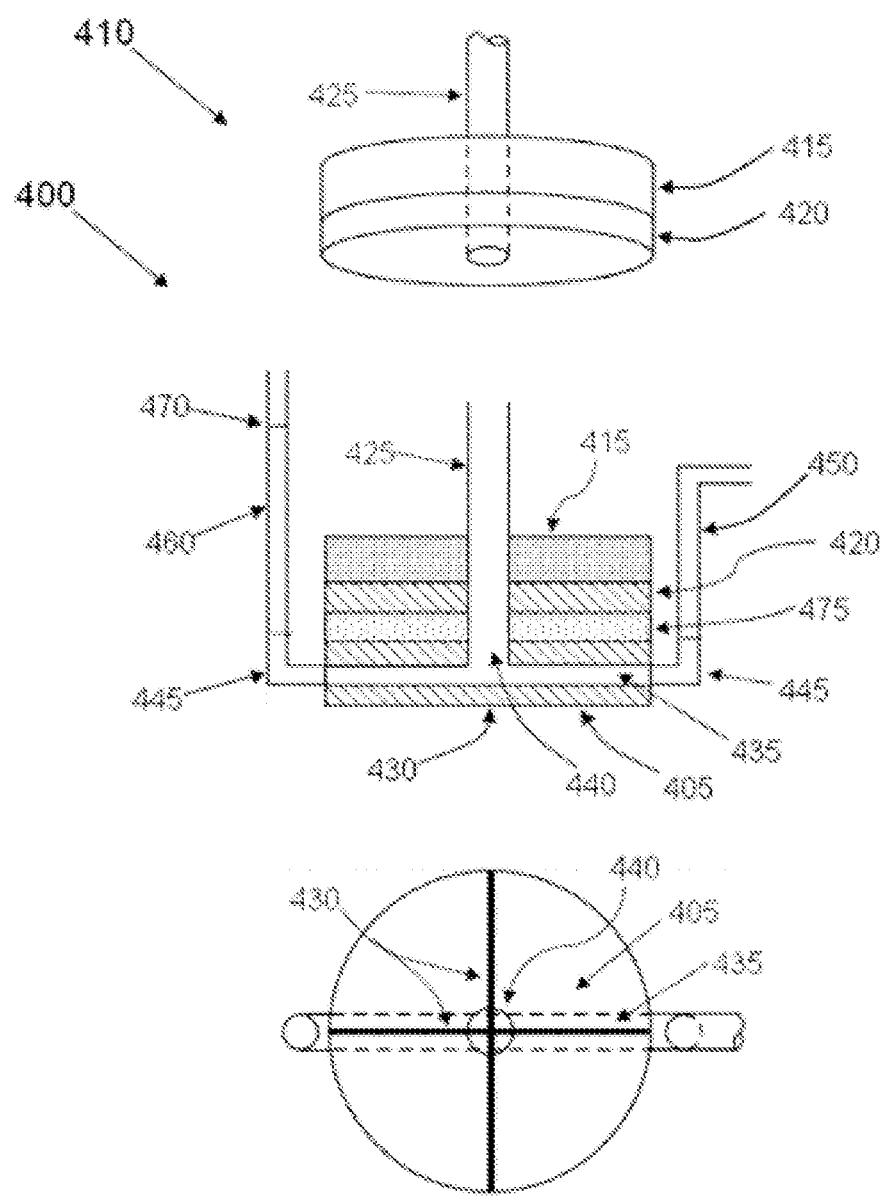
FIGS. 3 and 4 show partially schematic views of an equipment assembly used in the In-Plane Radial Permeability (IPRP) Test described herein.

The IPRP sample holder 400 is shown in FIG. 3 and comprises a cylindrical bottom plate 405, top plate 410, and cylindrical stainless steel weight 415.

Top plate 410 comprises an annular base plate 420, which is 9 mm thick with an outer diameter of 70 mm and a tube 425 of 150 mm length fixed at the center thereof. The tube 425 has an outer diameter of 15.8 mm and an inner diameter of 12 mm. The tube is adhesively fixed into a circular 16 mm hole in the center of the base plate 420 such that the lower edge of the tube is flush with the lower surface of the base plate, as depicted in FIG. 3. The bottom plate 405 and top plate 410 are fabricated from Lexan® or equivalent. The stainless steel weight 415 has an outer diameter of 70 mm and an inner diameter of 15.9 mm so that the weight is a close sliding fit on tube 425. The thickness of the stainless steel weight 415 is approximately 22 mm and is adjusted so that the total weight of the top plate 410 and the stainless steel weight 415 is 687 g±1 g to provide 2.0 kPa of confining pressure during the measurement.

Bottom plate 405 is approximately 25 mm thick and has two registration grooves 430 cut into the lower surface of the plate such that each groove spans the diameter of the bottom plate and the grooves are perpendicular to each other. Each groove is 1.5 mm wide and 2 mm deep. Bottom plate 405 has a horizontal hole 435 which spans the diameter of the plate. The horizontal hole 435 has a diameter of 8 mm and its central axis is 15 mm below the upper surface of bottom plate 405. Bottom plate 405 also has a central vertical hole 440 which has a diameter of 8 mm and is 10 mm deep. The central hole 440 connects to the horizontal hole 435 to form a T-shaped cavity in the bottom plate 405. The outer portions of the horizontal hole 435 are threaded to accommodate pipe elbows 445 which are attached to the bottom plate 405 in a watertight fashion. One elbow is connected to a vertical transparent tube 460 with a total height of 175 mm measured from the bottom of bottom plate 405 (including elbow 445) and an internal diameter of 6 mm. The tube 460 is scribed with a suitable mark 470 at a height of 100 mm above the upper surface of the bottom plate 420. This is the reference for the fluid level to be maintained during the measurement. The other elbow 445 is connected to the fluid delivery reservoir 700 (described below) via a flexible tube.

Figure 4:
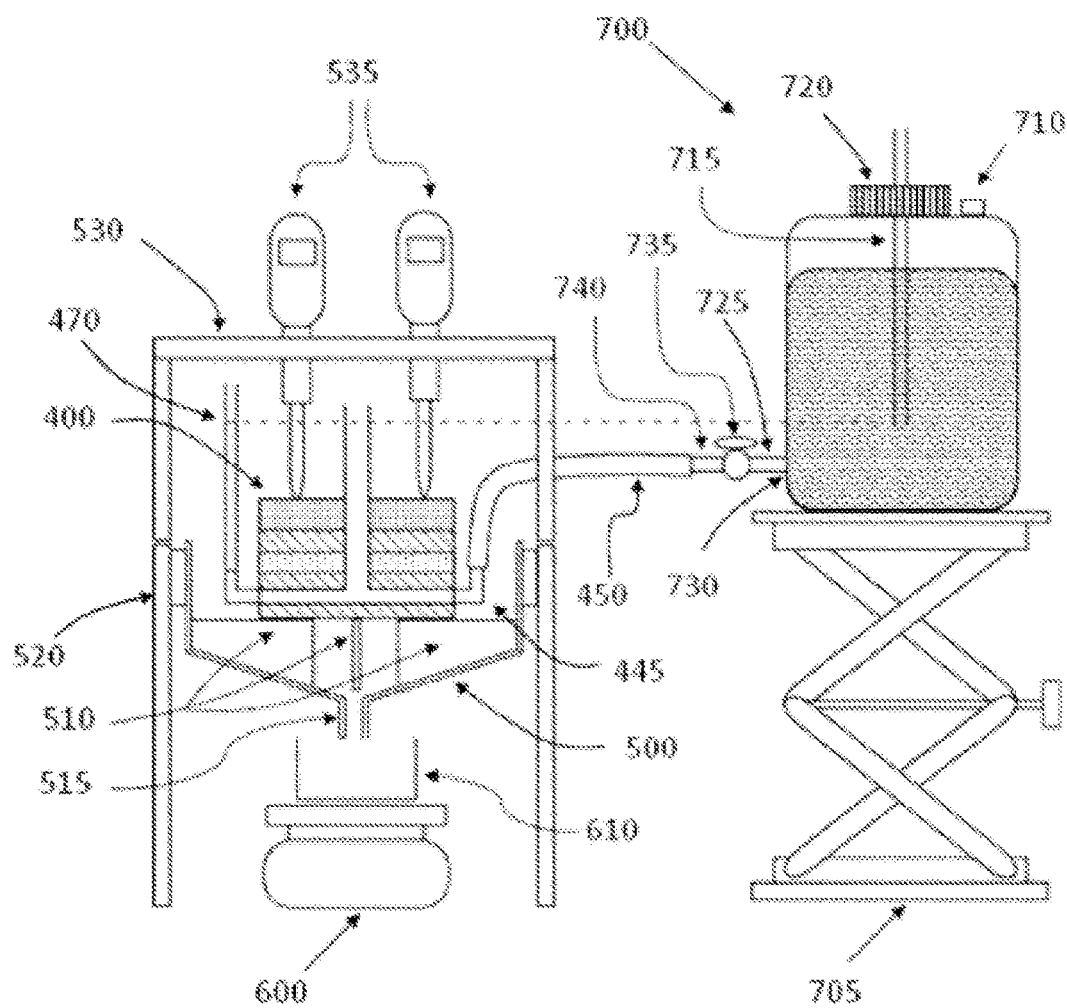

A suitable fluid delivery reservoir 700 is shown in FIG. 4. Reservoir 700 is situated on a suitable laboratory jack 705 and has an air-tight stoppered opening 710 to facilitate filling of the reservoir with fluid. An open-ended glass tube 715 having an inner diameter of 10 mm extends through a port 720 in the top of the reservoir such that there is an airtight seal between the outside of the tube and the reservoir. Reservoir 700 is provided with an L-shaped delivery tube 725 having an inlet 730 that is below the surface of the fluid in the reservoir, a stopcock 735, and an outlet 740. The outlet 740 is connected to elbow 445 via flexible plastic tubing 450 (e.g. Tygon®). The internal diameter of the delivery tube 725, stopcock 735, and flexible plastic tubing 450 enable fluid delivery to the IPRP sample holder 400 at a high enough flow rate to maintain the level of fluid in tube 460 at the scribed mark 470 at all times during the measurement. The reservoir 700 has a capacity of approximately 6 liters, although larger reservoirs may be required depending on the sample thickness and permeability. Other fluid delivery systems may be employed provided that they are able to deliver the fluid to the sample holder 400 and maintain the level of fluid in tube 460 at the scribed mark 470 for the duration of the measurement.

The IPRP catchment funnel 500 is shown in FIG. 4 and comprises an outer housing 505 with an internal diameter at the upper edge of the funnel of approximately 125 mm. Funnel 500 is constructed such that liquid falling into the funnel drains rapidly and freely from spout 515. A stand with horizontal flange 520 around the funnel 500 facilitates mounting the funnel in a horizontal position. Two integral vertical internal ribs 510 span the internal diameter of the funnel and are perpendicular to each other. Each rib 510 is 1.5 mm wide and the top surfaces of the ribs lie in a horizontal plane. The funnel housing 500 and ribs 510 are fabricated from a suitably rigid material such as Lexan® or equivalent in order to support sample holder 400. To facilitate loading of the sample it is advantageous for the height of the ribs to be sufficient to allow the upper surface of the bottom plate 405 to lie above the funnel flange 520 when the bottom plate 405 is located on ribs 510. A bridge 530 is attached to flange 520 in order to mount two digital calipers 535 to measure the relative height of the stainless steel weight 415. The digital calipers 535 have a resolution of ±0.01 mm over a range of 25 mm. A suitable digital caliper is a Mitutoyo model 543-492B or equivalent. Each caliper is interfaced with a computer to allow height readings to be recorded periodically and stored electronically on the computer. Bridge 530 has a circular hole 22 mm in diameter to accommodate tube 425 without the tube touching the bridge.

Funnel 500 is mounted over an electronic balance 600, as shown in FIG. 4. The balance has a resolution of ±0.01 g and a capacity of at least 1000 g. The balance 600 is also interfaced with a computer to allow the balance reading to be recorded periodically and stored electronically on the computer. A suitable balance is Mettler-Toledo model MS6002S or equivalent. A collection container 610 is situated on the balance pan so that liquid draining from the funnel spout 515 falls directly into the container 610.

The funnel 500 is mounted so that the upper surfaces of ribs 510 lie in a horizontal plane. Balance 600 and container 610 are positioned under the funnel 500 so that liquid draining from the funnel spout 515 falls directly into the container 610. The IPRP sample holder 400 is situated centrally in the funnel 500 with the ribs 510 located in grooves 430. The upper surface of the bottom plate 405 must be perfectly flat and level. The top plate 410 is aligned with and rests on the bottom plate 405. The stainless steel weight 415 surrounds the tube 425 and rests on the top plate 410. Tube 425 extends vertically through the central hole in the bridge 530. Both calipers 535 are mounted firmly to the bridge 530 with the foot resting on a point on the upper surface of the stainless steel weight 415. The calipers are set to zero in this state. The reservoir 700 is filled with 0.9% saline solution and re-sealed. The outlet 740 is connected to elbow 445 via flexible plastic tubing 450.

An annular sample 475 of the material to be tested is cut by suitable means. The sample has an outer diameter of 70 mm and an inner hole diameter of 12 mm. One suitable means of cutting the sample is to use a die cutter with sharp concentric blades.

The top plate 410 is lifted enough to insert the sample 475 between the top plate and the bottom plate 405 with the sample centered on the bottom plate and the plates aligned. The stopcock 735 is opened and the level of fluid in tube 460 is set to the scribed mark 470 by adjusting the height of the reservoir 700 using the jack 705 and by adjusting the position of the tube 715 in the reservoir. When the fluid level in the tube 460 is stable at the scribed mark 470 initiate recording data from the balance and calipers by the computer. Balance readings and time elapsed are recorded every 10 seconds for five minutes. The average sample thickness B is calculated from all caliper reading between 60 seconds and 300 seconds and expressed in cm. The flow rate in grams per second is the slope calculated by linear least squares regression fit of the balance reading (dependent variable) at different times (independent variable) considering only the readings between 60 seconds and 300 seconds.

Permeability k is then calculated by the following equation:

$$k = \frac{(Q/\rho_1) \cdot \mu \cdot \ln(R_0/R_i)}{2\pi \cdot B \cdot \Delta p} \quad (1)$$

Where:
k is the permeability (cm$^2$);
Q is the flow rate (g/s);
$\rho_1$ is the liquid density at 20° C. (g/cm$^3$);
$\mu$ is the liquid viscosity at 20° C. (Pa·s);
$R_0$ is the outer sample radius (cm);
$R_i$ is the inner sample radius (cm);
B is the average sample thickness (cm); and
$\Delta p$ is the pressure drop (Pa) calculated according to the following equation:

$$\Delta p = \left(\Delta h - \frac{B}{2}\right) \cdot g \cdot \rho_1 \cdot 10 \quad (2)$$

Where:
$\Delta h$ is the measured liquid hydrostatic pressure (cm);
g is the acceleration constant (m/sec$^2$); and
$\rho_1$ is the liquid density (g/cm$^3$).

IPRP is dependent on the fluid being used, so the IPRP value (in cm$^2$/MPa·sec) may be defined and calculated as follows:

$$\text{IPRP value} = (k/\mu) \quad (3)$$

Where:
k is the permeability (cm$^2$),
$\mu$ is the liquid viscosity at 20° C. (MPa·s).

MAP Analysis

Capillary pressure can be considered representative of a material's ability to wick fluid by capillary action and is expressed in the context of the present disclosure in terms of Medium Absorption Pressure (MAP), as explained below.

Figure 5:
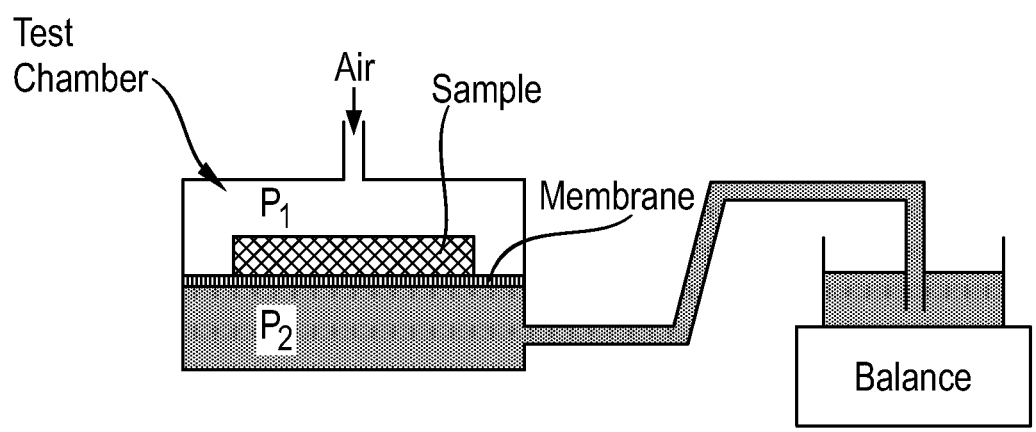
FIG. 5 shows a partially schematic view of an equipment assembly used in the Medium Absorption Pressure (MAP) Test described herein.

Capillary pressure measurements are made on a TRI/Autoporosimeter (TRI/Princeton Inc. of Princeton, N.J.). The TRI/Autoporosimeter is an automated computer-controlled instrument for measuring capillary pressure in porous materials, which can be schematically represented in FIG. 5. Complimentary Automated Instrument Software, Release Version 2007.6WD, is used to capture the data. More information on the TRI/Autoporosimeter, its operation and data treatments can be found in *The Journal of Colloid and Interface Science* 162 (1994), pp. 163-170, incorporated here by reference.

As used herein, determining capillary pressure hysteresis curve of a material as function of saturation, involves recording the increment of liquid that enters a porous material as the surrounding air pressure changes. A sample in the test chamber is exposed to precisely controlled changes in air pressure which at equilibrium (no more liquid uptake/release) corresponds to the capillary pressure.

The equipment operates by changing the test chamber air pressure in user-specified increments, either by decreasing pressure (increasing pore size) to absorb liquid, or increasing pressure (decreasing pore size) to drain liquid. The liquid volume absorbed (or drained) is measured with a balance at each pressure increment. The saturation is automatically calculated from the cumulative volume.

All testing is performed at 23° C.±2C.° and a relative humidity of 50%±5%. A saline solution of 0.9% weight to volume in deionized water is used. The surface tension (mN/m), contact angle (°), and density (g/cc) for all solutions are determined by any method known in the art. Alternatively (as done for measuring the Examples below), reference values for these parameters may be provided to the TRI/Autoporosimeter's software.

Surface tension (mN/m), contact angle (°), and density (g/cm$^3$) is provided to the instrument's software. Reference values used for the tests described herein were as follows: surface tension of 72 mN/m; contact angle of 0°; and liquid density of 1 g/cm$^3$. The balance is leveled at 156.7 g and equilibration rate set to 90 mg/min. The pore radius protocol (corresponding to capillary pressure steps) scans capillary pressures according to the following equation:

$$R = 2\gamma \cos \nu / \Delta p \quad (4)$$

Where:
R is the pore radius;
$\gamma$ is the surface tension;
$\nu$ is the contact angle; and
$\Delta p$ is the capillary pressure.

Tests are performed with the sample compressed with an applied load of approximately 0.3 psi. The weight applied to the sample is 428 g and is 50 mm in diameter.

The pressure sequence in Table 1, below, is applied to the measurement cell in the standard test protocol which corresponds to an individual pore radius as indicated.

TABLE 1

| | Height (mm) | Radius (μm) |
|---|---|---|
| 1 | 600 | 24.5 |
| 2 | 450 | 32.7 |
| 3 | 350 | 42.0 |
| 4 | 300 | 49.0 |
| 5 | 250 | 58.8 |
| 6 | 200 | 73.5 |
| 7 | 150 | 98.0 |
| 8 | 100 | 147 |
| 9 | 80 | 184 |
| 10 | 60 | 245 |
| 11 | 40 | 368 |
| 12 | 20 | 735 |
| 13 | 10 | 1470 |
| 14 | 20 | 735 |
| 15 | 40 | 368 |
| 16 | 60 | 245 |
| 17 | 80 | 184 |
| 18 | 100 | 147 |
| 19 | 150 | 98.0 |
| 20 | 200 | 73.5 |
| 21 | 250 | 58.8 |
| 22 | 300 | 49.0 |
| 23 | 350 | 42.0 |
| 24 | 450 | 32.7 |
| 25 | 600 | 24.5 |

The sample is cut into a circle with 5 cm diameter and then conditioned at 23° C.±2C.° and a relative humidity of 50%±5% for at least 24 hours before testing. The sample weight (to ±0.001 g) is measured. The empty sample chamber is closed. After the instrument has applied the appropriate air pressure to the cell, the liquid valve is closed and the chamber is opened. The specimen and confining weight are placed into the chamber and the chamber is closed. After the instrument has applied the appropriate air pressure to the cell, the liquid valve is opened to allow free movement of liquid to the balance and the test under the radius protocol is started. The instrument proceeds through one absorption/desorption cycle (also called a hysteresis loop). A blank (without specimen) is run in like fashion.

For calculations and reporting, the mass uptake from a blank run is directly subtracted from the uptake of the sample. Medium Absorption Pressure (MAP) is the pressure at which 50% of the liquid uptake has been achieved—or, in other words, the pressure that corresponds to 50% of the total liquid absorbed on the absorption branch of the hysteresis loop generated by the autoporosimeter.

EXAMPLES

The following examples summarize representative methods of treating cellulose fibers in accordance with the methods and concepts discussed above, and are illustrative in nature. The reagent amounts, times, conditions, and other process conditions may be varied from those disclosed in the specific representative procedures disclosed in the following examples without departing from the scope of the present disclosure.

Example 1: Grafting

Representative procedure: cellulose pulpsheets (CF416, 93% solids, Columbus Mill, from Weyerhaeuser NR Company, Federal Way, Wash.) were cut into rectangles (of 33.66 cm×10.16 cm (13.25"×4")), weighed, and placed into re-sealable plastic bags in pairs. A $Ce^{4+}$ catalyst solution was produced by stirring and dissolving a measured quantity of ammonium cerium(IV) sulfate (94%, from Sigma Aldrich) in 150.0 mL deionized water. Acrylic acid (99%, with 180-200 ppm MEHQ inhibitor, from Sigma Aldrich) in a measured volume was then added to the $Ce^{4+}$ solution and stirred for 5 minutes. The resulting solution was slowly poured over the cellulose pulpsheets, on both sides, in the bag, which was then sealed and allowed to equilibrate at room temperature overnight.

The sealed bag was then cured in a ventilated oven at 50° C. for 2 hours, followed by cooling to room temperature. The treated cellulose (cellulose-graft-poly(acrylic) acid) was then washed with 2.5 L deionized water in a Waring Blendor at low speed. Unreacted grafting solution, excess homopolymers of poly(acrylic) acid, and other impurities, were removed via vacuum filtration with Buchner funnel and filter paper, washed and vacuum filtered again, then oven-dried overnight at 50° C.

Graft yield was calculated using the following formula:

$$\% \text{ Graft Yield} = [(W_2 - W_1)/W_1] \times 100 \quad (5)$$

Where $W_1$=weight of starting cellulose material, and $W_2$=grafted product weight.

Representative data indicating weights and volumes used in a number of runs performed according to Example 1, and graft yields achieved, are shown in Table 2.

TABLE 2

| Run # | Wt Starting Material (g) | AA (mL) | Catalyst (g) | Wt Product (g) | Graft Yield (%) |
|---|---|---|---|---|---|
| 1 | 48.79 | 2.2 | 3.44 | 51.06 | 4.66 |
| 2 | 48.62 | 15.5 | 2.92 | 57.60 | 18.47 |
| 3 | 48.55 | 9.0 | 2.92 | 54.40 | 12.06 |
| 4 | 48.57 | 2.2 | 3.44 | 50.74 | 4.46 |
| 5 | 48.26 | 9.0 | 2.92 | 53.82 | 11.53 |
| 6 | 48.64 | 2.7 | 2.40 | 50.62 | 4.07 |
| 7 | 48.37 | 9.0 | 2.92 | 53.73 | 11.08 |
| 8 | 48.65 | 9.0 | 2.92 | 54.44 | 11.91 |
| 9 | 48.87 | 16.0 | 2.40 | 58.04 | 18.76 |
| 10 | 48.74 | 10.0 | 2.40 | 54.33 | 11.47 |
| 11 | 48.72 | 9.0 | 2.92 | 54.33 | 11.51 |
| 12 | 48.18 | 2.7 | 2.40 | 50.35 | 4.50 |
| 13 | 48.44 | 8.5 | 3.44 | 54.24 | 11.97 |
| 14 | 48.75 | 2.5 | 2.92 | 50.83 | 4.27 |
| 15 | 48.21 | 14.0 | 3.44 | 56.49 | 17.17 |
| 16 (control) | 48.92 | 0 | 0 | 49.04 | 0.25 |

A variety of cross-linking agents and reaction mechanisms were then applied to cellulose-graft-poly(acrylic) acid materials prepared in accordance with the procedure in Example 1, as described in Examples 2-7 infra.

Example 2: PAA Ester Cross-Linking

Representative procedure: using cellulose-graft-poly (acrylic) acid prepared according to the procedure in Example 1, 30.48 cm×30.48 cm (12"×12") British handsheets were prepared using all the material from one run (there was some loss during process). The handsheets were equilibrated to 93% solids in a humidity-controlled room. Each handsheet was cut into strips (of 30.48 cm×10.16 cm (12"×4")).

A polyacrylic acid ("PAA") crosslinking agent was applied (Aquaset™ 1676, available from the Dow Chemical Company; several examples of suitable PAA crosslinking agents are listed in U.S. Pat. App. Pub. No. 20110077354 of Stoyanov, et al.), in some cases in the presence of a sodium hypophosphite ("SHP") catalyst, to the handsheet strips. The treated strips were allowed to equilibrate, then air-dried, fiberized with a Kamas hammermill, and cured.

Representative data indicating weights and volumes used are shown in Table 3.

TABLE 3

| Run | Wt Handsheet @93% (g) | PAA % | PAA (g) |
|---|---|---|---|
| 1 | 53.05 | 0 | 0 |
| 2 | 59.16 | 1.5 | 1.49 |
| 3 | 56.40 | 0 | 0 |
| 4 | 52.78 | 3 | 2.96 |
| 5 | 55.70 | 1.5 | 1.47 |
| 6 | 52.68 | 0 | 0 |
| 7 | 55.58 | 1.5 | 1.48 |
| 8 | 56.38 | 3 | 2.97 |
| 9 | 60.01 | 0 | 0 |
| 10 | 56.31 | 1.5 | 1.49 |
| 11 | 56.34 | 1.5 | 1.49 |
| 12 | 52.37 | 3 | 2.94 |
| 13 | 56.19 | 1.5 | 1.48 |
| 14 | 52.86 | 1.5 | 1.49 |
| 15 | 58.35 | 0 | 0 |
| 16 (control) | 51.31 | 6.5 | 6.44 |

Example 3: Pentaerythritol Ester Cross-Linking

Representative procedure: using cellulose-graft-poly (acrylic) acid prepared according to the procedure in Example 1, an aqueous slurry was prepared using all the material from one run, which was then vacuum-filtered using a Buchner funnel to produce a pad. The pad was then oven-dried at 50° C. to constant weight.

A solution of 5.00 g pentaerythritol (from Sigma Aldrich) and 0.15 g sodium hypophosphite in 60 mL deionized water was prepared at 40° C., which was then cooled to room temperature and evenly applied to both sides of the pad via transfer pipette, and the treated pad was placed in a sealed plastic bag and allowed to equilibrate at room temperature overnight.

The pad was then fiberized in a Waring Blendor, and cured in an oven at 193° C. for 5 minutes.

Example 4: Trivalent Salt Ionic Cross-Linking

Representative procedure: using cellulose-graft-poly (acrylic) acid prepared according to the procedure in Example 1, an aqueous slurry was prepared using all the material from one run, which was then vacuum-filtered using a Buchner funnel to produce a pad. The pad was then air-dried to 43.5% solids content.

An aluminum sulfate solution was prepared by dissolving 10.00 g of aluminum sulfate octodecahydrate (from Sigma Aldrich) in 250 mL deionized water. The solution was evenly applied to both sides of the air-dried pad via transfer pipette, and the treated pad was placed in a sealed plastic bag and allowed to equilibrate at room temperature overnight.

The treated pad was then vacuum filtered in a Buchner funnel and gently rinsed, once, with 500 mL deionized water, then air-dried at room temperature until constant weight was achieved.

Example 5: Titanium-Based Ionic Cross-Linking

Representative procedure: using cellulose-graft-poly (acrylic) acid prepared according to the procedure in Example 1, an aqueous slurry was prepared using all the material from one run, which was then vacuum-filtered using a Buchner funnel to produce a pad. The pad was then oven-dried to constant weight.

A solution was prepared by dissolving 6.61 g of Tyzor® LA (lactic acid titanate chelate, from DuPont) in 26.4 mL deionized water at room temperature. The solution was evenly applied to both sides of the air-dried pad via transfer pipette, and the treated pad was placed in a sealed plastic bag and allowed to equilibrate at room temperature overnight.

The pad was then fiberized in a Waring Blendor, and cured in an oven at 175° C. for 15 minutes.

Example 6: Radical Cross-Linking

Representative procedure: using cellulose-graft-poly (acrylic) acid prepared according to the procedure in Example 1, 30.48 cm×30.48 cm (12"×12") British handsheets were prepared using 50 g of the material. The handsheets were equilibrated to 93% solids in a humidity-controlled room. Each handsheet was cut into strips (of 30.48 cm×10.16 cm (12"×4")).

A solution of 2.22 g of ammonium persulfate (from Sigma Aldrich) in 45 mL deionized water was prepared and evenly applied across the handsheet strips via transfer pipette, and the treated strips were placed in a sealed plastic bag and allowed to equilibrate at room temperature overnight.

The treated strips were then air-dried to about 70% solids and then fiberized with a Kamas hammermill. The material was then gently and evenly sprayed with 110 mL deionized water, placed in a foil pouch that was perforated to allow evaporation, and oven-cured at 199° C. (390° F.) for 15 minutes. After removal from the oven, the pouch was cooled to room temperature, and then the material was removed and allowed to air-dry at room temperature until constant weight was achieved.

Example 7: Ester Cross-Linking with Hyperbranched Polymers

Representative procedure: using cellulose-graft-poly (acrylic) acid prepared according to the procedure in Example 1, 30.48 cm×30.48 cm (12"×12") British handsheets were prepared using 50 g of the material. The handsheets were equilibrated to 93% solids in a humidity-controlled room. Each handsheet was cut into strips (of 30.48 cm×10.16 cm (12"×4")).

A solution of a measured quantity of a hyperbranched polymer (e.g., 0.22 g Lutensit® Z96 or 0.95 Lutensol® FP620, both from BASF) along with 0.14 g sodium hypophosphite in 45 mL deionized water was prepared and evenly applied across the handsheet strips via transfer pipette, and the treated strips were placed in a sealed plastic bag and allowed to equilibrate at room temperature overnight.

The treated strips were then air-dried to about 70% solids, fiberized with a Kamas hammermill, air-dried overnight, and cured at 187.8° C. (370° F.) for 5 minutes in a large dispatch oven.

AFAQ analysis was performed on the cellulose-graft-poly (acrylic) acid materials prepared in accordance the representative procedure of Example 1, as well as on various crosslinked cellulose-graft-poly(acrylic) acid materials prepared in accordance with the representative procedures of Examples 2-7. The representative values presented in Table 4 (below) are averages from multiple runs of the indicated crosslink method on the indicated graft yield % level of cellulose-graft-poly(acrylic) acid.

TABLE 4

| | AFAQ Analysis | | | | Sample Description | |
|---|---|---|---|---|---|---|
| Sample # | Wick Time sec | Wick Rate mm/s | Wet Bulk 0.6 kPa cm$^3$/g | Absorbent Capacity g/g | % graft | crosslink method |
| 1 | 2.1 | 9.42 | 9.73 | 9.93 | 11 | ionic (Al$^{3+}$) |
| 2 | 2.6 | 8.03 | 12.07 | 12.49 | 11 | ester (pentaerythritol) |
| 3 | 2.0 | 10.58 | 10.55 | 10.62 | 11 | titanium (Tyzor LA) |
| 4 | 4.6 | 6.63 | 16.53 | 16.74 | 12 | ester (PAA) |
| 5 | 4.0 | 6.89 | 11.19 | 11.32 | 6.6 | none |
| 6 | 3.8 | 8.43 | 15.92 | 15.83 | 6.6 | ester (HPB) |
| 7 | 3.8 | 7.12 | 10.93 | 11.01 | 11 | none |
| 8 | 3.7 | 6.32 | 11.26 | 11.56 | 11 | radical |
| 9 | 3.3 | 9.11 | 16.73 | 16.43 | 11 | ester (HPB) |
| 10 | 3.4 | 7.22 | 10.12 | 10.17 | 19.8 | none |
| 11 | 2.9 | 9.51 | 16.15 | 15.75 | 19.8 | ester (HPB) |
| 12 | 3.2 | 6.82 | 9.84 | 9.97 | 25.2 | none |
| 13 | 2.85 | 8.72 | 15.53 | 15.09 | 25.2 | ester (HPB) |
| Control A (CMC530) | 2.3 | 11.87 | 16.39 | 16.45 | n/a | n/a |

TABLE 4-continued

AFAQ Analysis

| Sample # | Wick Time sec | Wick Rate mm/s | Wet Bulk 0.6 kPa cm³/g | Absorbent Capacity g/g | Sample Description |  |
|---|---|---|---|---|---|---|
|  |  |  |  |  | % graft | crosslink method |
| Control B (CMC530) | 2.6 | 10.71 | 16.45 | 16.65 | n/a | n/a |
| Control C (CF416) | — | — | 11.71 | 11.75 | n/a | n/a |

Table 4 shows, for example, that cellulose-graft-poly (acrylic) acid produced from CF416 cellulose pulp fiber tends to exhibit lower wet bulk and absorbent capacity values as compared with untreated (i.e. non-grafted, non-crosslinked) CF416, across a range of graft yield levels tested. However, when subjected to subsequent crosslink treatment, the grafted, crosslinked cellulose structures produced thereby generally exhibited improved wet bulk values and/or absorbent capacity values. For example, ester crosslinking using PAA or a hyperbranched polymer as the cross-linking agent yielded improvements in wet bulk and absorbent capacity values, from about 6% to over 40%, as compared to untreated cellulose. Indeed, the improved values of these properties were found to be comparable with those exhibited by non-grafted, crosslinked cellulose samples (e.g., CMC530). Some crosslinking treatments, however, such as ionic trivalent salt and titanium-based reactions, did not increase, and in some cases further decreased, wet bulk and absorbent capacity values as compared to untreated cellulose. Also, in general, cellulose-graft-poly(acrylic) acid materials produced from CF416 exhibited lower wick rates than non-grafted, crosslinked cellulose samples, but when subjected to subsequent crosslink treatment, wick rates were seen to further decrease with some PAA/SHP and radical treatment processes, but increase with others (such as with ester cross-linking with HPB and pentaerythritol, and ionic processes). Thus, various absorbent properties may be modified through a selection of graft species, cross-linking reaction, and other process conditions.

Another performance metric by which the grafted, crosslinked cellulose materials produced in accordance with the present disclosure may be characterized and/or compared is by means of liquid permeability and capillary pressure, two properties important for absorbent products. Liquid permeability may be measured by in-plane radial permeability (IPRP) and capillary pressure may be measured by medium absorption pressure (MAP), according to the test methods described above.

As noted above, there is a trade-off between IPRP and MAP with known absorbent materials, including cellulose materials, synthetic fibers, blends, and so forth, in which IPRP tends to decrease as MAP increases. This trade-off is illustrated, for example, in FIG. 6, in the form of a dashed line following the least-squares best-fit curve that corresponds to IPRP and MAP values exhibited by example cellulose fiber controls, including crosslinked cellulose products such as CMC530 (used as a control in the Examples and subsequent AFAQ analysis described above) as well as non-crosslinked cellulose products such as NB416, CF416, and so forth. The IPRP and MAP values are shown in Table 5, below. The curve can be described mathematically as a power law function $y=mx^z$, with IPRP value as the abscissa and MAP as the ordinate. For the Table 5 data, the best-fit curve for the non-grafted controls can be expressed by the formula $y=896.38x^{-0.549}$, with $R^2=0.9479$.

TABLE 5

| IPRP Value (cm²/MPa · sec) | MAP (cm H₂O) | Material |
|---|---|---|
| 594 | 21.3 | non-crosslinked control |
| 651 | 23.9 |  |
| 736 | 23.7 |  |
| 737 | 25.6 |  |
| 759 | 31.6 |  |
| 2144 | 12.9 | crosslinked control |
| 2360 | 12.3 |  |
| 2674 | 11.8 |  |
| 2723 | 11.5 |  |
| 3061 | 11.6 |  |
| 3219 | 10.3 |  |
| 3453 | 9.7 |  |
| 3659 | 10.6 |  |
| 3708 | 9.8 |  |
| 4350 | 9.0 |  |
| 5189 | 8.1 |  |
| 5296 | 8.0 |  |

Figure 6:
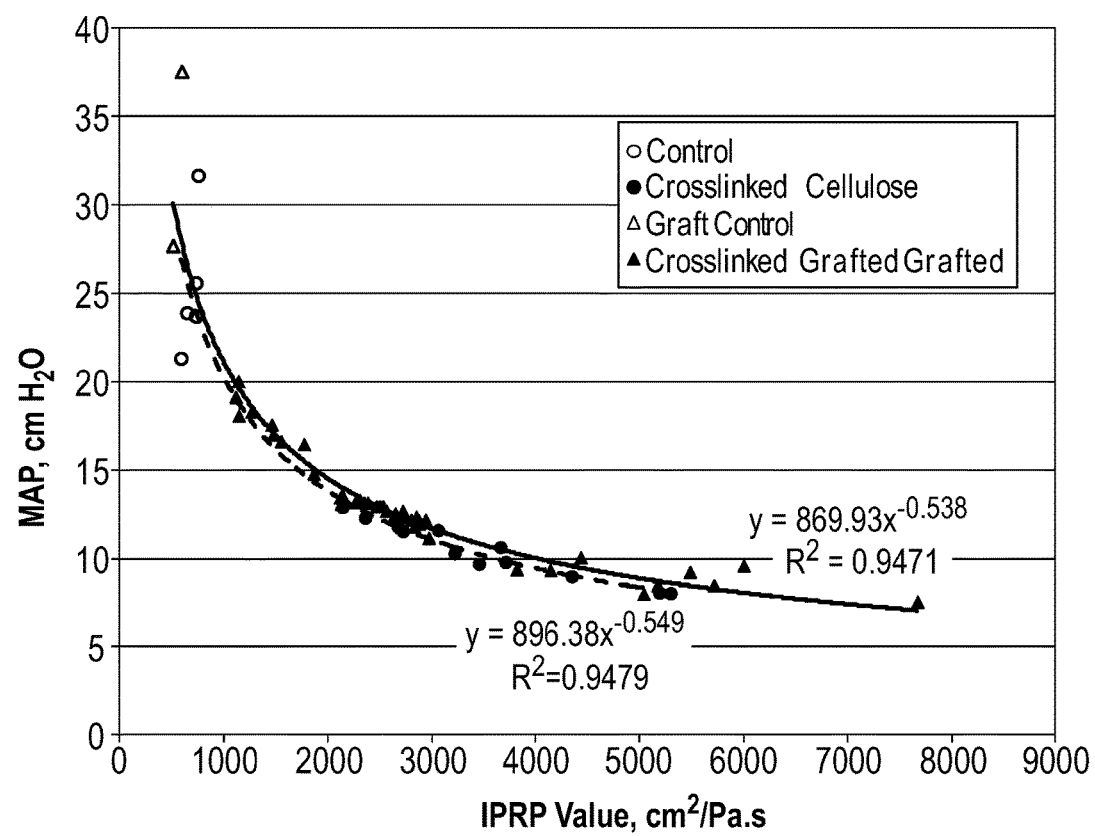
FIG. 6 is a graph comparing best-fit curves showing the relationship between MAP and IPRP values exhibited by example embodiments of grafted cellulose materials produced in accordance with the present disclosure (including crosslinked as well as non-crosslinked cellulose materials, collectively represented as the solid line) and example non-grafted cellulose materials (including crosslinked as well as non-crosslinked cellulose materials, collectively represented by the dashed line).

As exemplified, for example, in FIG. 6 (and Table 5), cellulose fibers have been observed to be bounded by a maximum IPRP value of about 5400 cm²/MPa·sec and a maximum MAP value of about 32 cm H₂O. Higher IPRP values have been achieved, but only with blends of cellulose with synthetic fibers (e.g. polyethylene, polypropylene and/or polyester fibers) or synthetic nonwovens produced from, for example, polyethylene, polypropylene and/or polyester fibers or filaments.

Focusing in particular on crosslinked cellulose fibers, such products have been observed to be bounded by a maximum MAP value of about 13 cm H₂O.

The grafted, crosslinked cellulose materials prepared in accordance with the present disclosure, however, exhibit IPRP values as high as 7700 cm²/MPa·sec and MAP values up to 20 cm H₂O.

In some examples, IPRP and MAP values for grafted, crosslinked cellulose materials approximate a trade-off curve that is slightly shifted (i.e. raised) and also elongated (i.e. spans a broader IPRP range), with respect to that exhibited by the non-grafted cellulose controls, as shown in FIG. 6. The trade-off for the grafted materials is shown as a solid line following the best-fit curve for the example data presented in Table 6, below.

TABLE 6

| IPRP Value (cm²/MPa · sec) | MAP (cm H₂O) | Material |
|---|---|---|
| 517 | 27.67 | grafted, non-crosslinked |
| 601 | 37.55 |  |
| 1113 | 19.13 | grafted, crosslinked |
| 1139 | 20.02 |  |
| 1143 | 18.06 |  |
| 1267 | 18.31 |  |
| 1465 | 17.56 |  |
| 1479 | 17.01 |  |
| 1555 | 16.62 |  |
| 1774 | 16.45 |  |
| 1868 | 14.79 |  |
| 2122 | 13.44 |  |
| 2129 | 13.09 |  |
| 2139 | 13.58 |  |
| 2152 | 13.34 |  |
| 2270 | 13.17 |  |
| 2270 | 13.20 |  |

TABLE 6-continued

| IPRP Value (cm²/MPa · sec) | MAP (cm H₂O) | Material |
|---|---|---|
| 2308 | 13.31 | |
| 2384 | 13.13 | |
| 2386 | 13.16 | |
| 2470 | 12.95 | |
| 2502 | 12.95 | |
| 2532 | 12.94 | |
| 2564 | 12.69 | |
| 2649 | 12.55 | |
| 2651 | 12.45 | |
| 2710 | 11.78 | |
| 2714 | 12.33 | |
| 2722 | 12.69 | |
| 2801 | 12.18 | |
| 2832 | 11.80 | |
| 2851 | 12.36 | |
| 2875 | 12.15 | |
| 2879 | 11.98 | |
| 2940 | 12.20 | |
| 2971 | 11.16 | |
| 3816 | 9.39 | |
| 4143 | 9.34 | |
| 4434 | 10.07 | |
| 5038 | 8.00 | |
| 5483 | 9.24 | |
| 5713 | 8.49 | |
| 5999 | 9.61 | |
| 7672 | 7.55 | |

The best-fit curve generated by the example data set in Table 6, corresponding to grafted cellulose materials, can be expressed by the formula $y=869.93x^{-0.538}$ (with $R^2=0.9471$). Best-fit curves for example materials prepared in accordance with the present disclosure can be characterized by the same general power law function represented by the formula $y=mx^z$, with m values ranging from about 600 to about 1200 (and more particularly from about 800 to about 1100), and z values ranging from about −0.590 to −0.515 (and more particularly from about −0.560 to about −0.520). These best-fit curve models for the grafted materials of the present disclosure correspond to or predict the IPRP value for a given MAP value (and vice versa) within about +/−30% of the value of x (or y) in the respective formula, particularly at IPRP values y (in cm²/MPa·sec) ranging from about 1000 to about 7700.

Comparing the best-fit curves for the example non-grafted controls (dashed line) and the example grafted materials (solid line), the "shift" visible in FIG. 4 (and shown by the data in Tables 5 and 6) illustrates that, in the range of IPRP values exhibited by non-grafted cellulose fiber control materials (that is, a range of from about 600 to about 5400 cm²/MPa·sec), the example grafted materials exhibit (or are predicted to exhibit) MAP values equal to or higher than the corresponding MAP values possessed by non-grafted cellulose materials. Also, for a given MAP value (in cm H₂O) in a range of from about 7.0 to about 25, the grafted materials exhibit (or are predicted to exhibit) IPRP values equal to or higher than the corresponding IPRP values possessed by non-grafted cellulose fiber. Focusing specifically on the data corresponding to crosslinked materials, the difference in IPRP values is generally up to about 20% higher for the example grafted materials as compared to the example non-grafted controls over an MAP range of about 7.0 to 20 (although the differences are even greater in some instances, for example with IPRP values exhibited at MAP values between about 7.0 and about 10), and the difference in MAP values is generally up to 15% higher for grafted materials over arrange of IPRP values of about 800 to 5400 cm²/MPa·sec.

Comparing the best-fit curves for the example non-grafted controls and the example grafted materials, the "elongation" visible in FIG. 6 (and shown by the data in Tables 5 and 6) illustrates that IPRP values greater than those achieved with non-grafted cellulose products (e.g., IPRP values greater than about 5400 cm²/MPa·sec) are exhibited by the grafted, crosslinked cellulose materials of the present disclosure.

Accordingly, the grafted, crosslinked cellulose of the present disclosure may have suitability, for example, in absorbent applications similar to those for which non-grafted, crosslinked cellulose fibers are used, as well as other applications.

Although the inventive subject matter for which protection is sought is defined in the appended claims, other illustrative, non-exclusive examples of inventive subject matter relating to absorbent articles and methods of making such articles according to the present disclosure are described in the following enumerated paragraphs:

A. An absorbent article comprising cellulosic material, the cellulosic material comprising a cellulose fiber and polymer chains composed of at least one monoethylenically unsaturated acid group-containing monomer grafted thereto, wherein one or more of the cellulose fiber and the polymer chains are crosslinked.

A.1. The absorbent article of A, wherein the cellulose fiber is wood fiber.

A.2. The absorbent article of A or A.1, wherein the cellulosic material includes mainly intra-fiber crosslinks.

A.3. The absorbent article of any of A through A.2, wherein, in the in cellulosic material, the at least one monoethylenically unsaturated acid group-containing monomer includes one or more of acrylic acid, maleic acid, and methacrylic acid.

A.4. The absorbent article of any of A through A.3, wherein, in the cellulosic material, the at least one monoethylenically unsaturated acid group-containing monomer is acrylic acid.

A.5. The absorbent article of any of A through A.4, wherein the cellulosic material is characterized by a graft yield of 5-35 weight %.

A.6. The absorbent article of any of A through A.5, wherein the cellulosic material is characterized by a graft yield of 10-20 weight %.

A.7. The absorbent article of any of A through A.6, wherein the cellulosic material has a wet bulk at least 6% greater than untreated cellulose fiber.

A.8. The absorbent article of any of A through A.7, wherein the cellulosic material has a wet bulk at least 40% greater than untreated cellulose fiber.

A.9. The absorbent article of any of A through A.8, wherein the cellulosic material has a wet bulk of about 10.0-17.0 cm³/g.

A.10. The absorbent article of any of A through A.9, wherein the cellulosic material has a wet bulk of about 15.0-17.0 cm³/g.

A.11. The absorbent article of any of A through A.10, wherein the cellulosic material has an absorbent capacity of about 10.0-17.0 g/g.

A.12. The absorbent article of any of A through A.11, wherein the cellulosic material has an absorbent capacity of about 15.0-17.0 g/g.

A.13. The absorbent article of any of A through A.12, wherein the cellulosic material has an IPRP value of about 1000 to 7700 cm²/MPa·sec and a MAP of about 7.0 to 20 cm H₂O.

A.14. The absorbent article of any of A through A.13, wherein, for the cellulosic material, for a given IPRP value y (in cm²/MPa·sec) from 1000 to 7700, the MAP value of the cellulosic material (in cm H₂O) is within +/−30% of the value of x in the formula $y=mx^z$; wherein m is from 600 to 1200, and wherein z is from −0.590 to −0.515.

A.15 The absorbent article of A.14, wherein z is from −0.560 to −0.520.

A.16. The absorbent article of A.14 or A.15, wherein m is from 800 to 1100.

A.17. The absorbent article of any of A through A.16, wherein the cellulosic material is characterized in that at a given IPRP value (in cm²/MPa·sec) from 800 to 5400, the material has a MAP value that is equal to or higher than the corresponding MAP value possessed by non-grafted, cross-linked cellulose fiber, the non-grafted, cross-linked cellulose fiber being the same cellulose fiber as the cellulose fibers comprised by cellulosic material prior to grafting.

A.18. The absorbent article of A.17, wherein the cellulosic material at the given IPRP value has a MAP value that is between 0 and 20% higher than the corresponding MAP value possessed by non-grafted, crosslinked cellulose fiber, the non-grafted, cross-linked cellulose fiber being the same cellulose fiber as the cellulose fibers comprised by cellulosic material prior to grafting.

A.19. The absorbent article of any of A through A.17, wherein the cellulosic material is characterized in that at a given MAP value (in cm H₂O) from 7.0 to 20, the cellulosic material has an IPRP value that is equal to or higher than the corresponding IPRP value possessed by non-grafted, cross-linked cellulose fiber, the non-grafted, cross-linked cellulose fiber being the same cellulose fiber as the cellulose fibers comprised by cellulosic material prior to grafting.

A.20. The absorbent article of A.19, wherein the cellulosic material at the given MAP value has an IPRP value that is between 0 and 15% higher than the corresponding IPRP value possessed by non-grafted, crosslinked cellulose fiber the non-grafted, cross-linked cellulose fiber being the same cellulose fiber as the cellulose fibers comprised by cellulosic material prior to grafting.

A.21. The absorbent article of any of A through A.12, wherein the cellulosic material has an IPRP value of 5400 cm²/MPa·sec or above.

B. An absorbent article comprising fibrous cellulosic material, the fibrous cellulosic material comprising cellulose-graft-poly(acrylic) acid having a graft yield of 10-20 weight % and wherein two or more grafted polymer chains of poly(acrylic) acid are intra-fiber crosslinked.

B.1. The absorbent article of B, wherein the fibrous cellulosic material has a wet bulk of about 15.0-17.0 cm³/g.

B.2. The absorbent article of B or B.1, wherein, in the fibrous cellulosic material, the two or more polymer chains of poly(acrylic) acid are intra-fiber crosslinked by a hyperbranched polymer.

B.3. The absorbent article of any of B through B.2, wherein, in the fibrous cellulosic material, the two or more polymer chains of poly(acrylic) acid are intra-fiber cross-linked by pentaerythritol.

C. Use of a grafted, crosslinked cellulosic material in an absorbent article, wherein the grafted, crosslinked cellulosic material has been made by method comprising (a) grafting polymer chains of at least one monoethylenically unsaturated acid group-containing monomer from a cellulosic substrate to produce a grafted cellulosic material, and (b) subsequently crosslinking the grafted cellulosic material by treating the material with a crosslinking agent adapted to effect crosslinking of one or more of the cellulosic substrate or the polymer chains.

C.1. The use of C, wherein the cellulosic material is cellulose fiber.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a cellulosic material, the cellulosic material comprising a cellulose fiber and polymer chains composed of at least one monoethylenically unsaturated acid group-containing monomer; wherein the polymer chains composed of at least one monoethylenically unsaturated acid group-containing monomer are grafted to the cellulosic fiber; wherein, in one or more of the cellulose fiber, the polymer chains are intra-fiber crosslinked to the cellulose fiber; wherein the absorbent article comprises a distribution layer; wherein the distribution layer comprises at least 50% by weight of the cellulosic material; wherein, in the cellulosic material, the graft yield is from about 10% by weight to about 20% by weight; wherein, in the cellulosic material, the at least one monoethylenically unsaturated acid group-containing monomer includes acrylic acid;

wherein the cellulosic material has a wet bulk at least about 6% greater than untreated cellulose fiber, the untreated cellulose fiber being the same cellulosic fiber as the cellulosic fiber used for making the cellulosic material; and wherein the cellulosic material has a wet bulk of about 15.0-17.0 cm³/g.

2. The absorbent article of claim 1, wherein the cellulosic material has an In Plane Radial Permeability (IPRP) value of about 1000 to 7700 cm²/MPa·sec and a Medium Absorption Pressure (MAP) of about 7.0 to 20 cm H₂O.

3. The absorbent article of claim 1, wherein at a given IPRP value (in cm²/MPa·sec) from about 800 to about 5400, the cellulosic material has a MAP value that is equal to or higher than the corresponding MAP value possessed by the non-grafted, crosslinked cellulose fiber.

4. The absorbent article of claim 1, wherein at a given MAP value (in cm H₂O) from about 7.0 to about 20, the cellulosic material has an IPRP value that is equal to or higher than the corresponding IPRP value possessed by the non-grafted, crosslinked cellulose fiber.

5. The absorbent article of claim 1, wherein the cellulosic material has an IPRP value of about 5400 $cm^2$/MPa·sec or above.

6. The absorbent article of claim 1, wherein the absorbent article is selected from the group consisting of a diaper, a pant, a sanitary napkin and a pantiliner, wherein the absorbent article comprises a topsheet, a backsheet, an absorbent core disposed between the topsheet and backsheet, and an optional acquisition-distribution system disposed between the topsheet and the absorbent core, and wherein the grafted, crosslinked cellulosic material is comprised by the absorbent core and/or by the optional acquisition-distribution system.

7. The absorbent article of claim 6, wherein the grafted crosslinked cellulosic material forms all of the acquisition-distribution system or forms a layer of the acquisition-distribution system.

8. An absorbent article comprising a fibrous cellulosic material, the fibrous cellulosic material comprising cellulose-graft-poly(acrylic) acid having a graft yield of about 10-20 weight %, wherein two or more grafted polymer chains of poly(acrylic) acid are intra-fiber crosslinked; wherein the absorbent article comprises a distribution layer; wherein the distribution layer comprises at least 50% by weight of the fibrous cellulosic material;
 wherein the fibrous cellulosic material has a wet bulk at least about 6% greater than untreated cellulose fiber, the untreated cellulose fiber being the same cellulosic fiber as the cellulosic fiber used for making the fibrous cellulosic material; and
 wherein the fibrous cellulosic material has a wet bulk of about 15.0-17.0 $cm^3$/g.

9. The absorbent article of claim 8, wherein the two or more polymer chains of poly(acrylic) acid are intra-fiber crosslinked by one or more of pentaerythritol and a hyperbranched polymer.

* * * * *